(12) United States Patent
Miller (10) Patent No.: US 9,259,302 B2
(45) Date of Patent: Feb. 16, 2016

(54) PRESSURE SENSING ELECTRIC TOOTHBRUSH

(71) Applicant: KONINKLIJKE PHILIPS N.V., Eindhoven (NL)

(72) Inventor: Kevin Arnold Miller, Bellevue, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/652,810

(22) PCT Filed: Dec. 18, 2013

(86) PCT No.: PCT/IB2013/061060
§ 371 (c)(1),
(2) Date: Jun. 17, 2015

(87) PCT Pub. No.: WO2014/102667
PCT Pub. Date: Jul. 3, 2014

(65) Prior Publication Data
US 2015/0297327 A1    Oct. 22, 2015

Related U.S. Application Data

(60) Provisional application No. 61/746,633, filed on Dec. 28, 2012.

(51) Int. Cl.
*A46B 15/00* (2006.01)
*A61C 17/22* (2006.01)

(52) U.S. Cl.
CPC ........... *A61C 17/221* (2013.01); *A46B 15/0012* (2013.01); *A46B 15/0038* (2013.01)

(58) Field of Classification Search
CPC ........... A46B 15/0012; A46B 15/0038; A61C 17/221
See application file for complete search history.

(56) References Cited

U.S. PATENT DOCUMENTS 5,815,872 A * 10/1998 Meginniss, III ... A46B 15/0002
15/105
2003/0000032 A1   1/2003 Lev

FOREIGN PATENT DOCUMENTS

| EP | 0158870 A1 | 10/1985 |
| EP | 1228737 A2 | 8/2002 |
| WO | 9700650 A1 | 1/1997 |
| WO | 2014037856 A1 | 3/2014 |
| WO | 2014335899 A1 | 3/2014 |

* cited by examiner

*Primary Examiner* — Randall Chin

(57) ABSTRACT

The toothbrush includes a sensor system for determining pressure on the teeth by a direct force measurement such as displacement, and a system for determining pressure on the teeth by a dynamic load measurement system, such as phase shift. These different pressure results are combined with peak-to-peak bristle motion values of Hall effect output values and compared to a table to obtain a more accurate value of bristle pressure against the teeth and to raise, lower or maintain the trigger threshold of excessive pressure accordingly.

13 Claims, 8 Drawing Sheets

PRESSURE SENSING ELECTRIC TOOTHBRUSH

CROSS-REFERENCE TO PRIOR APPLICATIONS

This application is the U.S. National Phase application under 35 U.S.C. §371 of International Application No. PCT/IB2013/061060, filed on Dec. 18, 2013, which claims the benefit of U.S. Provisional Patent Application No. 61/746,633, filed on Dec. 28, 2012. These applications are hereby incorporated by reference herein.

TECHNICAL FIELD

This invention relates generally to power toothbrushes with bristle pressure sensors, and more specifically concerns such a toothbrush with improved pressure sensing accuracy.

BACKGROUND OF THE INVENTION

The use of a pressure sensor is well known in power toothbrushes. Such sensors, also referred to as load sensors, actually measure force, in grams, which the bristle field applies to the teeth. However, the results of such sensors typically include other types of loads, such as loads produced by the cheek, tongue and lips, in addition to direct bristle force against the teeth produced by user action. An accurate indication of bristle pressure against the teeth, apart from the other loads, would provide better information for the user as well as adapt the appliance for better effectiveness.

Accordingly, it is desirable to provide a pressure/force sensing system which provides more accurate information to the user concerning the application of excessive force.

SUMMARY OF THE INVENTION

Accordingly, a power toothbrush with a pressure sensor comprises: a system for determining pressure applied against a user's teeth by bristles of the toothbrush by a direct force measurement; a system for determining pressure applied against the user's teeth by the bristles of the toothbrush by a dynamic force measurement and a processing system responsive to the pressure determined by the direct force measurement and the dynamic force measurement to adjust the pre-established amount of pressure indicative of excessive bristle force.

BEST MODE FOR CARRYING OUT THE INVENTION

There are several types of loads which are produced by tissues in the mouth during brushing action in addition to pressure on the teeth by toothbrush bristles. There is a spring load which is produced by action of the bristles against the teeth. There is also a damping action, in the form of friction, which occurs between the cheek against the bristle plate supporting the toothbrush bristles, the bristles against the teeth, the tongue against the bristle plate and the lips against the neck of the toothbrush, Still further, there is a load produced by the cheek against the bristle plate, as well as the teeth against the bristles, the lips against the bristle plate, the tongue against the bristle plate, the bristles against the teeth and the teeth against the bristles.

Figure 1:
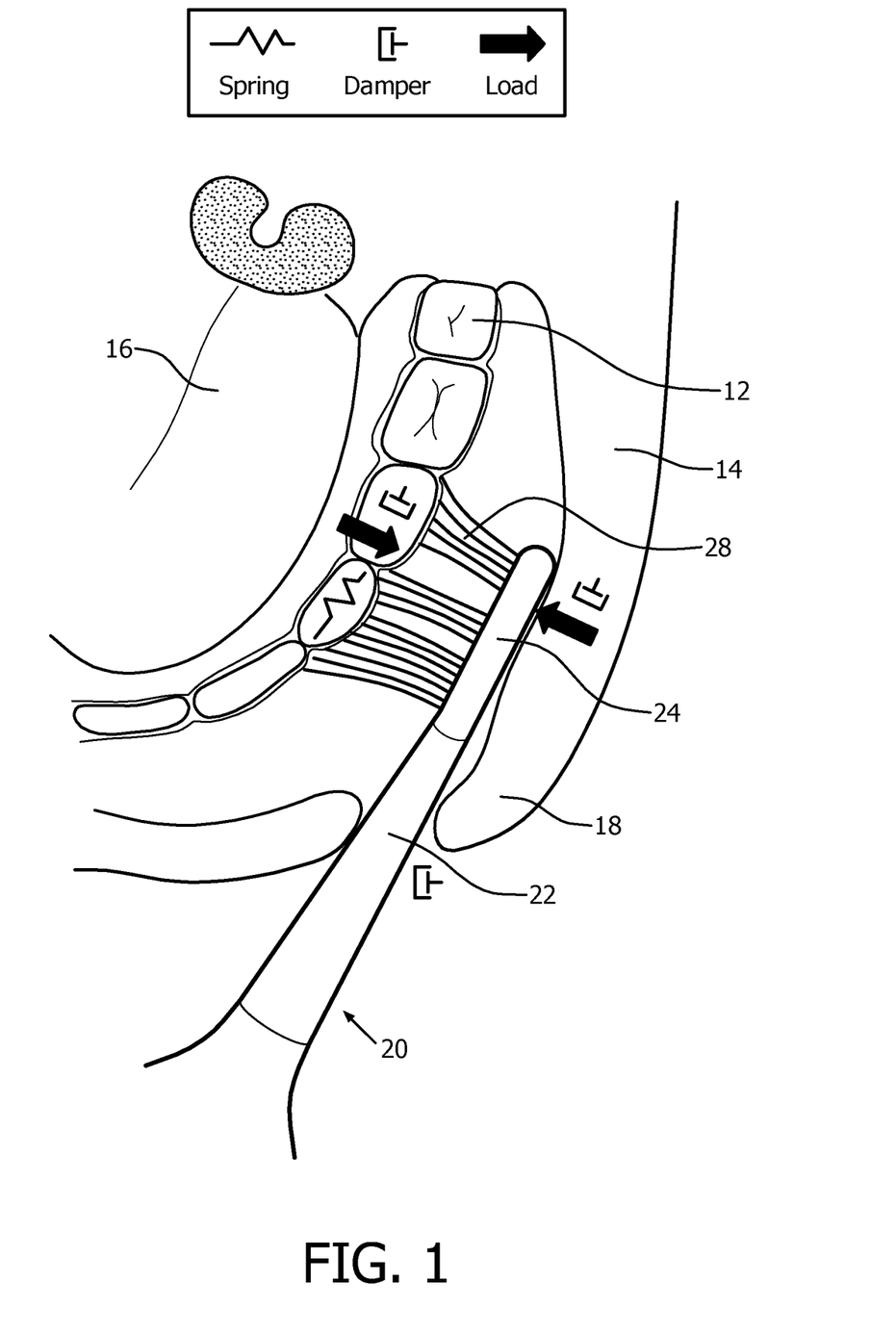
FIG. 1 is a plan view of various portions of the mouth of a user and a toothbrush when the exterior (buccal) surfaces of the teeth are being brushed.
Figure 2:
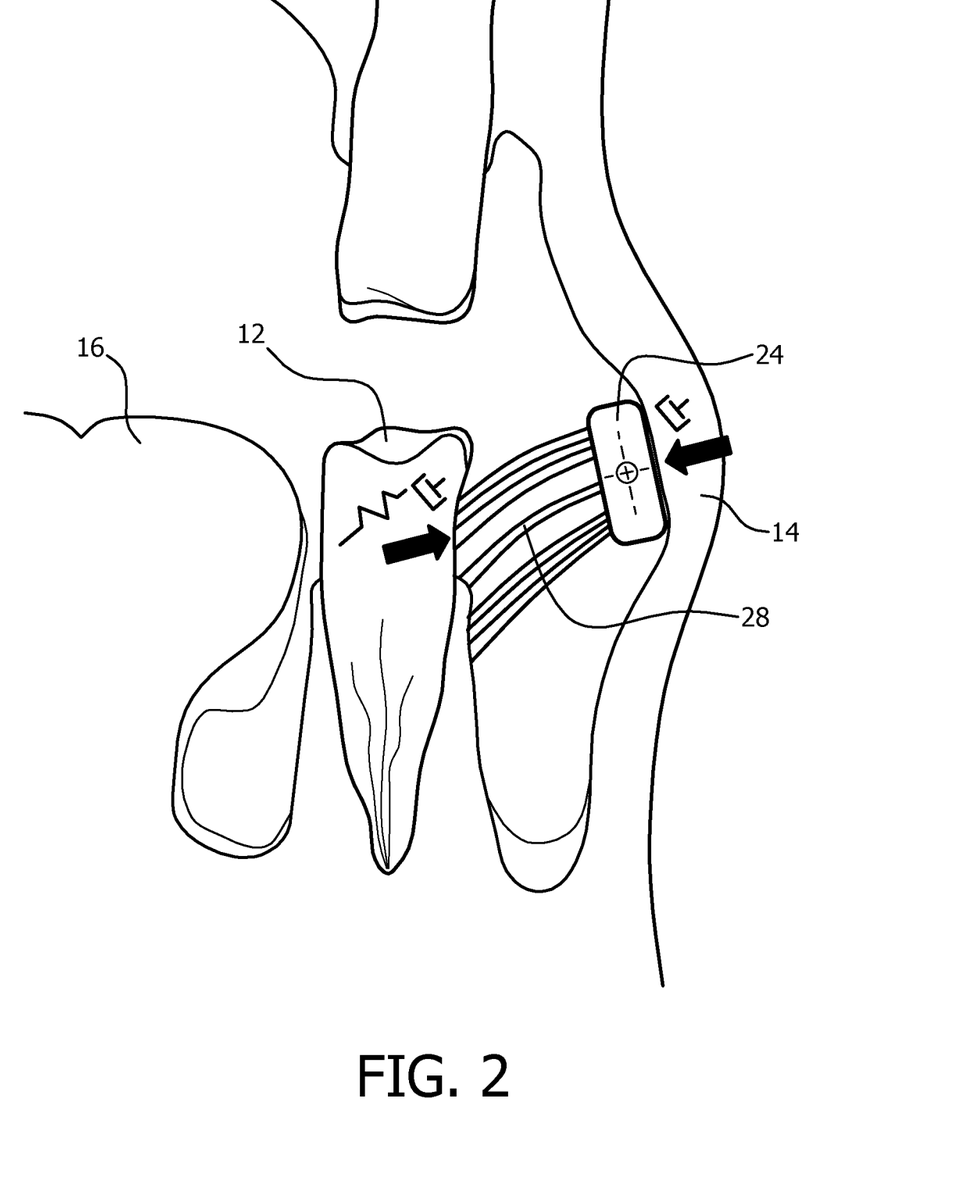
FIG. 2 is an elevational view of FIG. 1.
Figure 3:
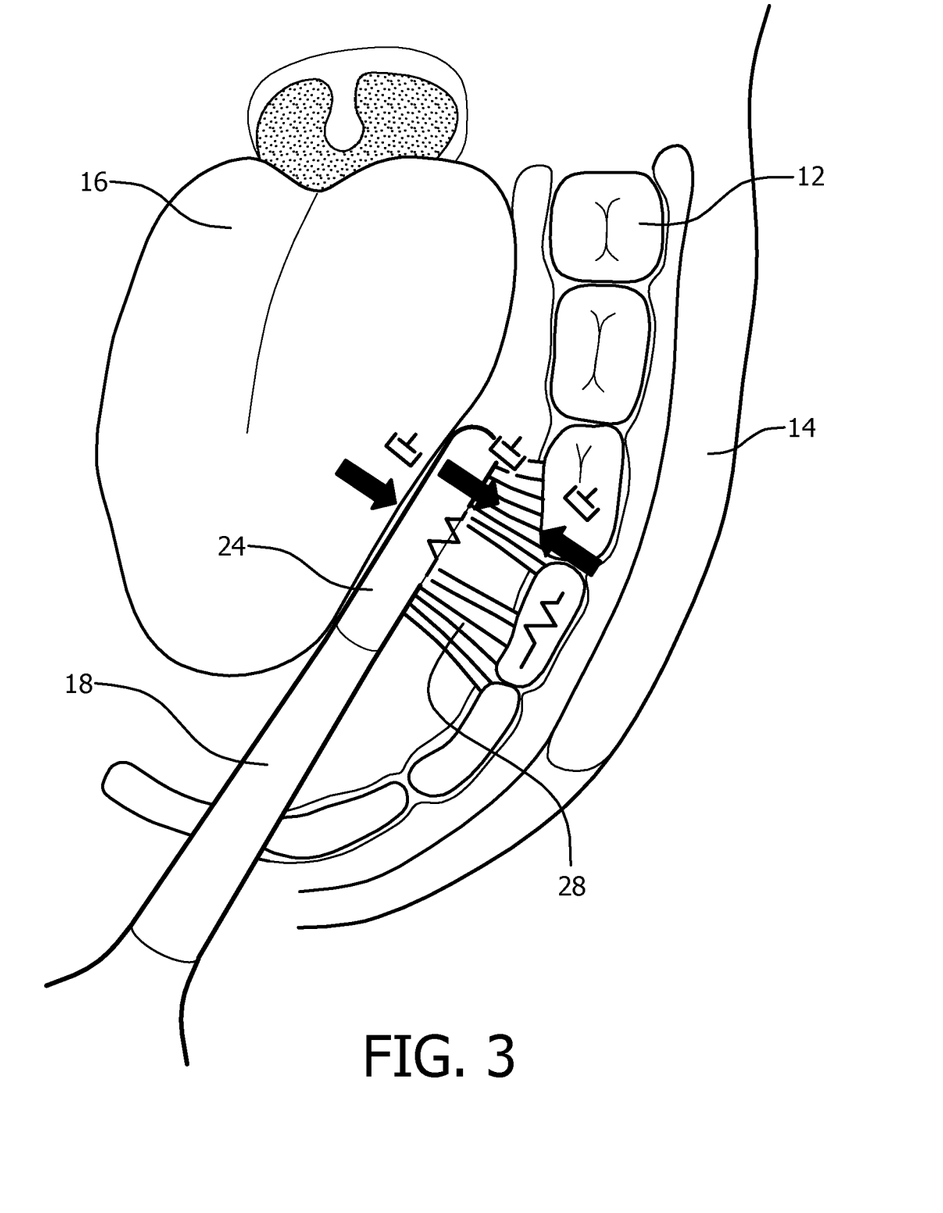
FIG. 3 is a plan view of the mouth of a user and a toothbrush when the interior (lingual) surfaces of the teeth are being brushed.
Figure 4:
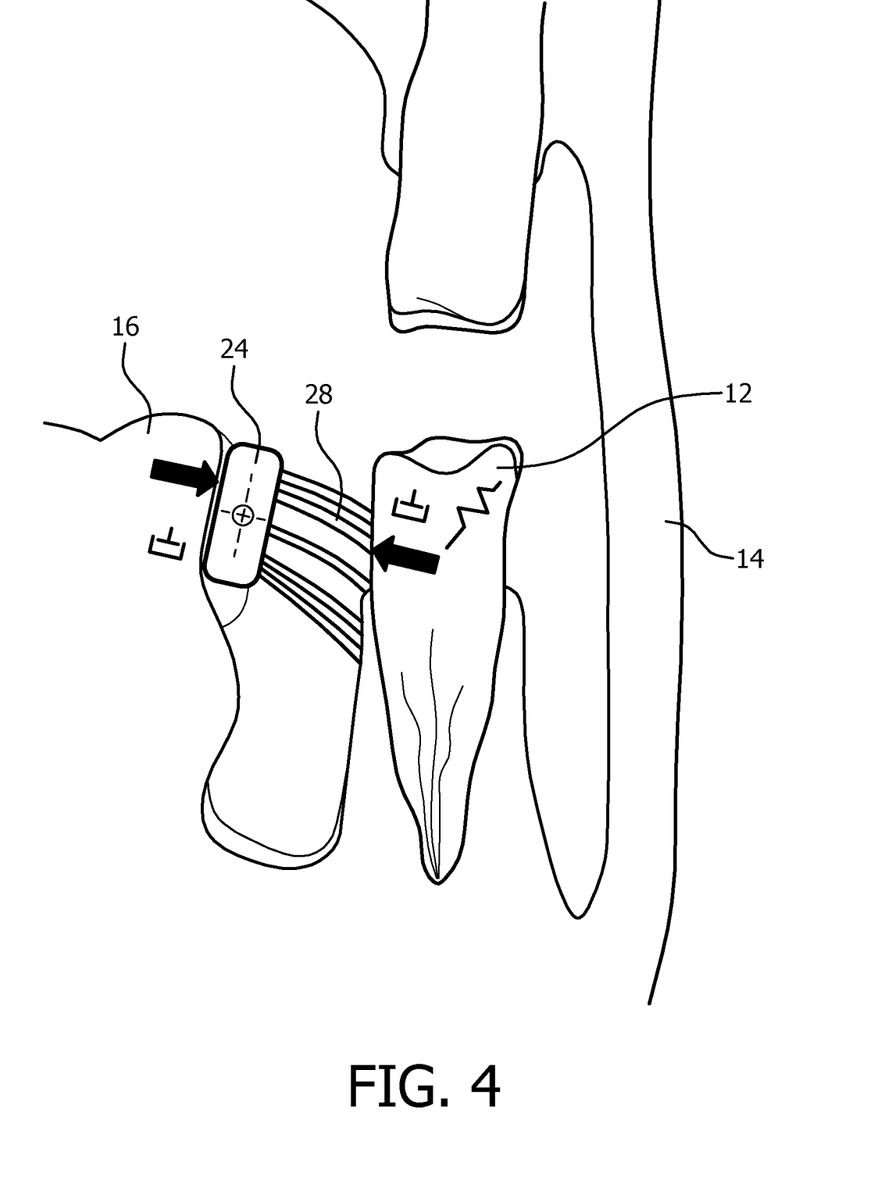
FIG. 4 is a top view of the mouth of FIG. 3.
Figure 5:
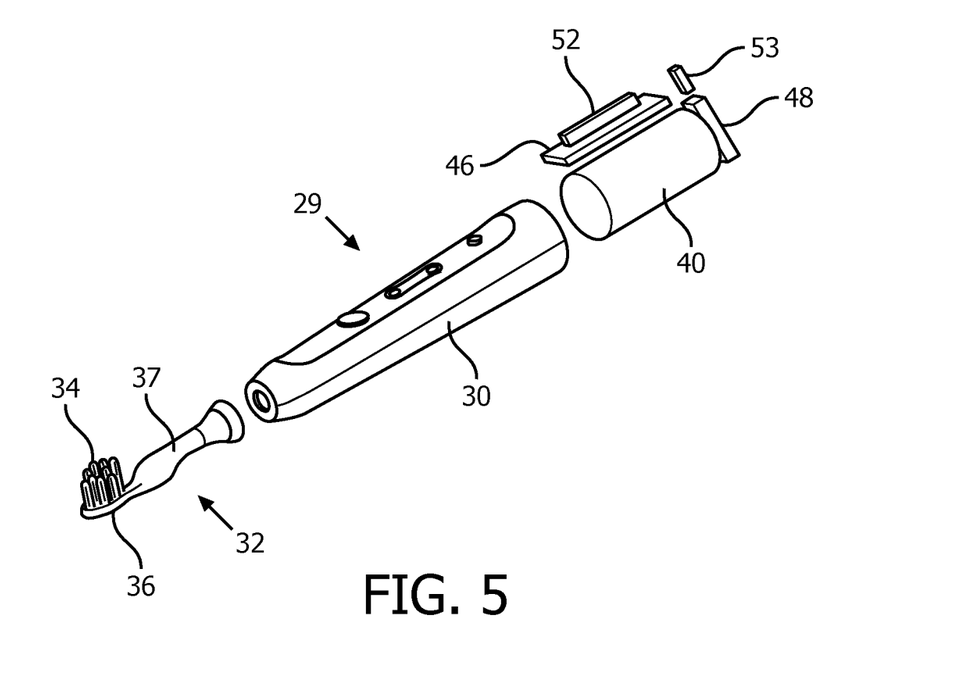
FIG. 5 is a simplified diagram of a portion of a toothbrush producing pressure information.

These various loads are illustrated in FIGS. 1 and 2 for the exterior (buccal) surfaces of the teeth, while FIGS. 3 and 4 show the load for the interior (lingual) surfaces. The teeth are illustrated at 12, the cheek is shown at 14, the tongue at 16 and the lips at 18. The toothbrush is shown generally at 20, with a neck portion of the toothbrush shown at 22, a bristle plate portion at 24, and the bristles at 28. Pressure sensor systems, attempting to measure force/load of the bristles against the teeth in order to provide to the user information concerning the application of excessive force relative to possible pressure on it, as well as minimum force for cleansing effectiveness, such sensors, however, actually measure more than just bristle pressure against the teeth and therefore provide somewhat inaccurate information to the user relative to excessive pressure. In particular, due to the inclusion of certain mouth tissue loads in addition to direct bristle pressure against the teeth, the trigger point (threshold) for producing the excessive pressure indication to the user may be too high or too low. If too high, harm may be caused without warning, and if too low, effectiveness can be decreased.

The present invention is designed to provide more accurate and informed trigger point information to the user, in particular more accurate/definitive information concerning the pressure or force applied to the surface of the teeth by the bristles. In the present invention, two different force determination systems are used and the information obtained from each system is used relative to a table to affect the information provided to the user relative to a possible overload or excessive pressure. For example, if a trigger point is set at 300 grams in the processor, the information provided by the two different pressure sensor systems, as well as information concerning peak-to-peak values, is used to adjust the pre-set value at which a warning is provided to the user. One pressure sensing system provides direct force or displacement information, while the other sensing system provides dynamic force information.

There are several sensing arrangements which provide a direct force or displacement information and arrangements which provide dynamic force information, as well as peak-to-peak information.

In the present arrangement, the direct force or displacement information is provided by a Hall effect sensor arrangement, while the dynamic load information is provided also by a Hall effect sensor used to measure phase shift between the magnetic field response relative to the phase of the drive signal. Other arrangements can be used, however, to provide the displacement and dynamic load sensing information.

FIG. 1 shows a simplified view of a power toothbrush arranged to include a Hall effect sensing arrangement to produce both displacement and dynamic load information. The power toothbrush shown generally at 29 includes a handle 30, a brushhead assembly 32 and a set of bristles 34, with a bristle plate 36 positioned at the distal end of a neck portion 37 of the brushhead assembly. The brushhead assembly is typically removable from the handle portion. The power toothbrush includes a drive train assembly shown very generally at 40 powered by a rechargeable battery. The power toothbrush further includes a microprocessor 46 which produces the drive signal for the drive train and also processes the signal information from the Hall effect sensor/sensors to provide displacement and dynamic load information. At the rear of drive train 40 is a magnet 48. In the embodiment shown, the magnet has the following dimensions: 13.4 mm by 9.0 mm by 4.0 mm. One example of a suitable magnet is neodymium. Other magnets can be used. Mounted within the power toothbrush is a Hall-effect sensor or sensors 52. The Hall-effect sensors 52 can be mounted in various positions within the power toothbrush. In one embodiment, one Hall-effect sensor is mounted on a flex circuit which is attached to the printed circuit board containing the microprocessor, so that the Hall-effect sensor can respond to a changing magnetic field as the toothbrush moves in operation. This results in a dynamic force determination, as explained below.

Another Hall-effect sensor 53 can be mounted on the drive train frame of the toothbrush located approximately 2.3 mm from the magnet, in approximately the same plane thereof. This Hall-effect sensor recognizes the lateral displacement of the drive train due to force on the bristle field against the teeth, mounted or arranged, such as in a V-spring embodiment, so that the rear end of the drive train moves laterally in response to user force.

In operation, relative to the direct force (displacement) information as the rear end of the drive train and the magnet swing back and forth through a selected angle, the voltage output of Hall-effect sensor 53 varies sinusoidally. The voltage output of the Hall-effect sensor will vary in accordance to a changing magnetic field. The changing magnet field provides a basis for determining the amount of force applied to the bristles relative to displacement. As force is applied to the bristle field, the rear end of the drive train pivots, including the magnet, producing a lateral displacement of the magnet in the direction of the Hall-effect sensor. The Hall-effect sensor is sensitive enough to detect a change in the magnetic field as the magnet comes closer to the sensor. The microprocessor in the toothbrush includes a table of information in the form of a response curve which relates to the voltage output of the Hall-effect sensor to the displacement of the magnet and hence the force applied to the brush element. The displacement of the magnet will result in a change of voltage output of the Hall-effect sensor relative to the voltage output under no-load conditions. Accordingly, the change in the sensor output is a reliable indication of the displacement force being applied to the bristle field. Reference is made herein to U.S. Provisional Patent Application No. 61/695,396, which concerns a direct-force (displacement) pressure information system for a toothbrush.

With respect to the generation of dynamic load information, a sinusoidal output is also produced by the Hall-effect sensor under no-load conditions. In this arrangement, the Hall-effect sensor detects a change in phase between the drive signal for the appliance and the mechanical response of the brushhead assembly produced by movement of the magnet 48 as pressure on the bristle field changes. As pressure increases the phase shift increases. Typically, the change in phase will be linear over a defined change of pressure (force), such as from 0 grams to at least 300 grams, at which point the pressure has typically exceeded a maximum value for comfort and effectiveness. Information is also stored in the microprocessor which specifically relates phase shift information and values to force applied, for the particular appliance being tested, so that a specific phase shift is accurately indicative of pressure/force applied to the bristle field of that toothbrush, specifically the dynamic force.

The drive signal is typically a square wave, which in one cycle rises from a zero level to a positive value and after a time determined by the drive frequency declines to a value of opposing polarity, which drive signal cycle continues for the duration of operation of the toothbrush for each event. In the embodiment shown, the drive frequency is 250 Hz, and the amplitude of motion is between 9-11°. This is, however, only one example of operation. The frequency and amplitude may be varied.

The toothbrush is initially calibrated to determine a time offset which exists between the square wave motor drive signal and the mechanical response signal, as indicated by the signal output from the Hall sensor. This is done under no-load conditions, so that the static phase relationship between the motor drive signal and the response signal is known and can be in effect a zero set for signal processing during actual operation of the toothbrush.

Figure 6:
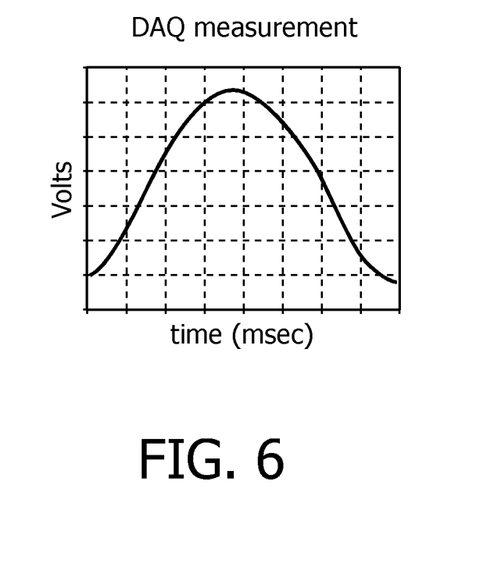
FIG. 6 is an output of a half-cycle of a Hall effect sensor with an output signal calibrated to the drive signal for the appliance.
Figure 7:
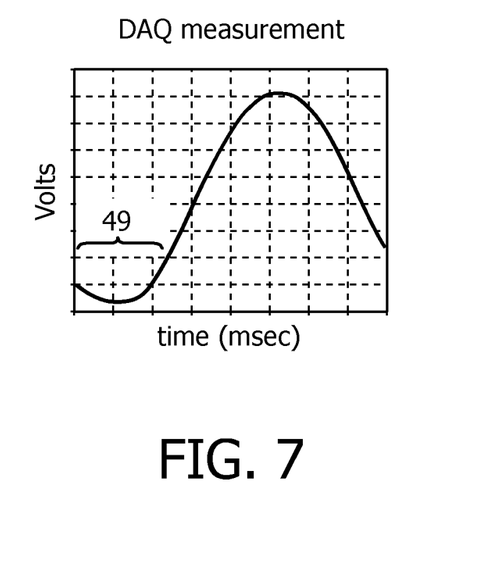
FIG. 7 is a diagram similar to that of FIG. 6 showing a phase shift in the output signal due to load.

FIG. 6 shows a single half-cycle of the response signal (Hall sensor output) with the left-hand edge of the signal synchronized to the rising edge of the motor drive signal. As pressure/load is applied to the bristle field, there will be a phase shift in the Hall sensor output signal relative to the motor drive signal. One example of a phase shift (49) is illustrated in FIG. 7.

The value of the phase shift is determined continuously as load is applied to the bristle field. There are many ways to determine phase shift. One is by determining zero crossing. As the phase shifts, the zero crossing of the response signal from the Hall sensor will shift in direct proportion. The zero threshold is determined by averaging the signal over a number of cycles. The time from the start of the motor drive cycle to the first transition of the sensor signal through this zero threshold is then measured. The zero crossing provides an indication of the phase shift.

Another possibility for obtaining phase shift information is by a quadrature sampling process, in which four samples are used per cycle to extract the DC offset and phase of a sine wave. Four samples are taken 90° apart, in the calculation below by $S_1$, $S_2$, and $S_4$. The average voltage, or the DC offset, can be calculated:

$$V_0 = \frac{S_1 + S_3}{2} = \frac{S_2 + S_4}{2}$$

The signals will typically include noise, so that multiple samples are typically averaged to smooth results. To calculate the phase, two samples of in-phase and quadrature phase are defined as follows:

$$I = \frac{S_1}{V_0} \text{ and } Q = \frac{S_2}{V_0}$$

with the phase angle being defined as:

$$\theta = \operatorname{atan2}\left(\frac{1}{Q}\right)$$

Averaging I and Q over multiple samples is effective to reduce noise.

The above are just two examples of determining phase shift. Other techniques can be used as well.

Reference is made to Provisional Patent Application No. 61/698,078, which is directed toward a dynamic load (phase shift) sensing arrangement.

Figure 8:
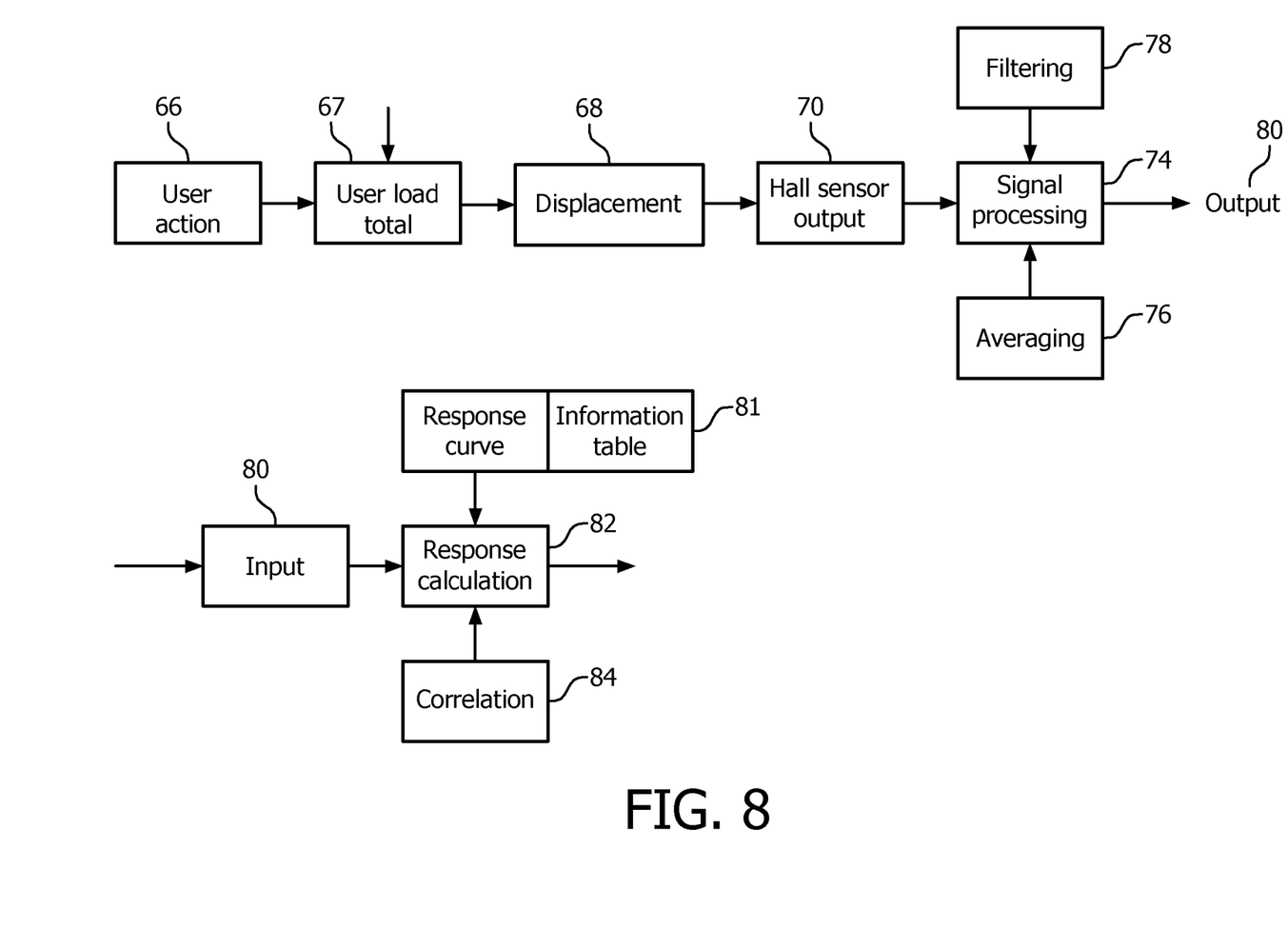
FIG. 8 is a processing diagram producing direct force information from the sensor of FIG. 5.

FIG. 8 shows the processing of the direct force (displacement) signal information. The user action is represented at block 66, indicating the amount of force actually applied by the user. The total load action is represented at 67, which includes loads other than bristle pressure on the teeth. The displacement produced at the rear end of the drive train and the magnet is represented by block 68. The displacement produces a signal from the Hall-effect sensor as represented by block 70. The Hall-effect output signal is then processed at block 74, determining the change in the voltage and output due to the total load. The processing includes averaging the output over a number of cycles, referred to at 76, as well as filtering noise from the signal, including electronic noise and mechanical noise from the motor, which is represented at 78. The result is an output signal 80 which is the input signal to the remainder of the processing circuit. As indicated above, the microprocessor includes a response curve or table of information 81 which relates Hall-effect sensor output to a particular displacement force value. The response curve is typically a straight line for an average of 0-300 grams of force. This calculation will include a correlation step represented at 84, which involves correlation of force and Hall sensor values over the force range. Information is provided continuously.

Figure 9:
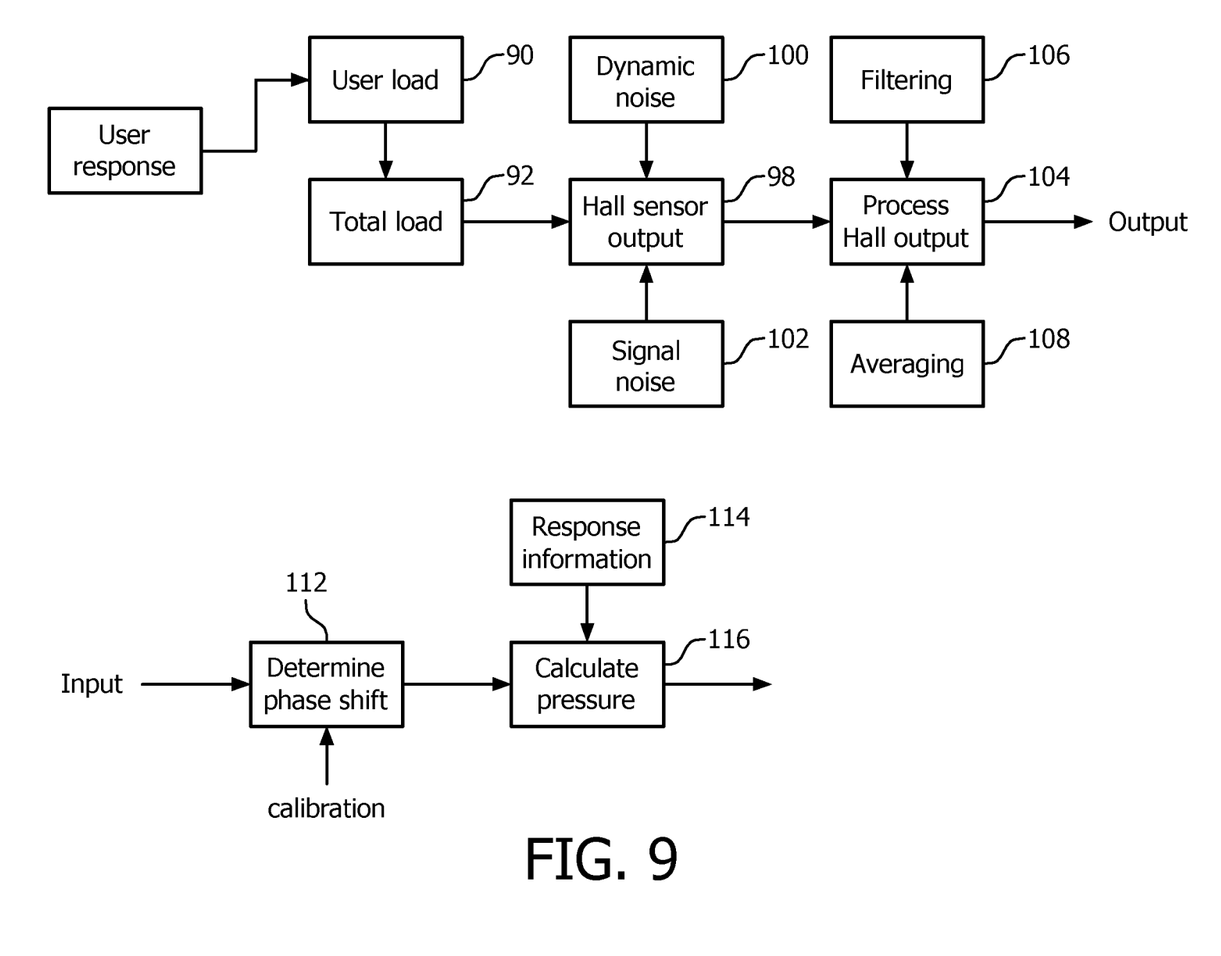
FIG. 9 is a processing diagram for determining dynamic force information from the sensor of FIG. 5.

The Hall-effect dynamic load (phase shift) sensing system (FIG. 9) also includes generally the pressure applied by the user. 90 as well a total load 92 which occurs during brushing. The total dynamic load creates phase shift between the motor drive signal and the Hall sensor output signal which represents the response of the system. The Hall sensor output is shown at 98. The sensor output signal is affected by signal noise 100 which can be from various sources including the Hall sensor itself as well as variations in mounting or a change in the resonant system over time. Hall sensor output is also sensitive to dynamic noise 100, which typically is produced by the vibration from a drive train. The Hall sensor output is then processed at 104, which can include filtering 106 and averaging 108 to produce a clean output signal. This signal represented as output 104 is subject to further processing. The actual phase shift is determined at 112. As indicated above, the phase shift can be determined by a standard zero crossing circuit or by other arrangements. The phase shift is determined for a calibrated appliance. The processor uses the phase shift to calculate the dynamic pressure by use of stored information 114 which relates phase shift along one axis to pressure along the other axis. The pressure resulting from the phase shift circuit is shown at 116.

Peak-to-peak movement of the bristle motion can also be determined by one or the other pressure measurement systems.

Figure 10:
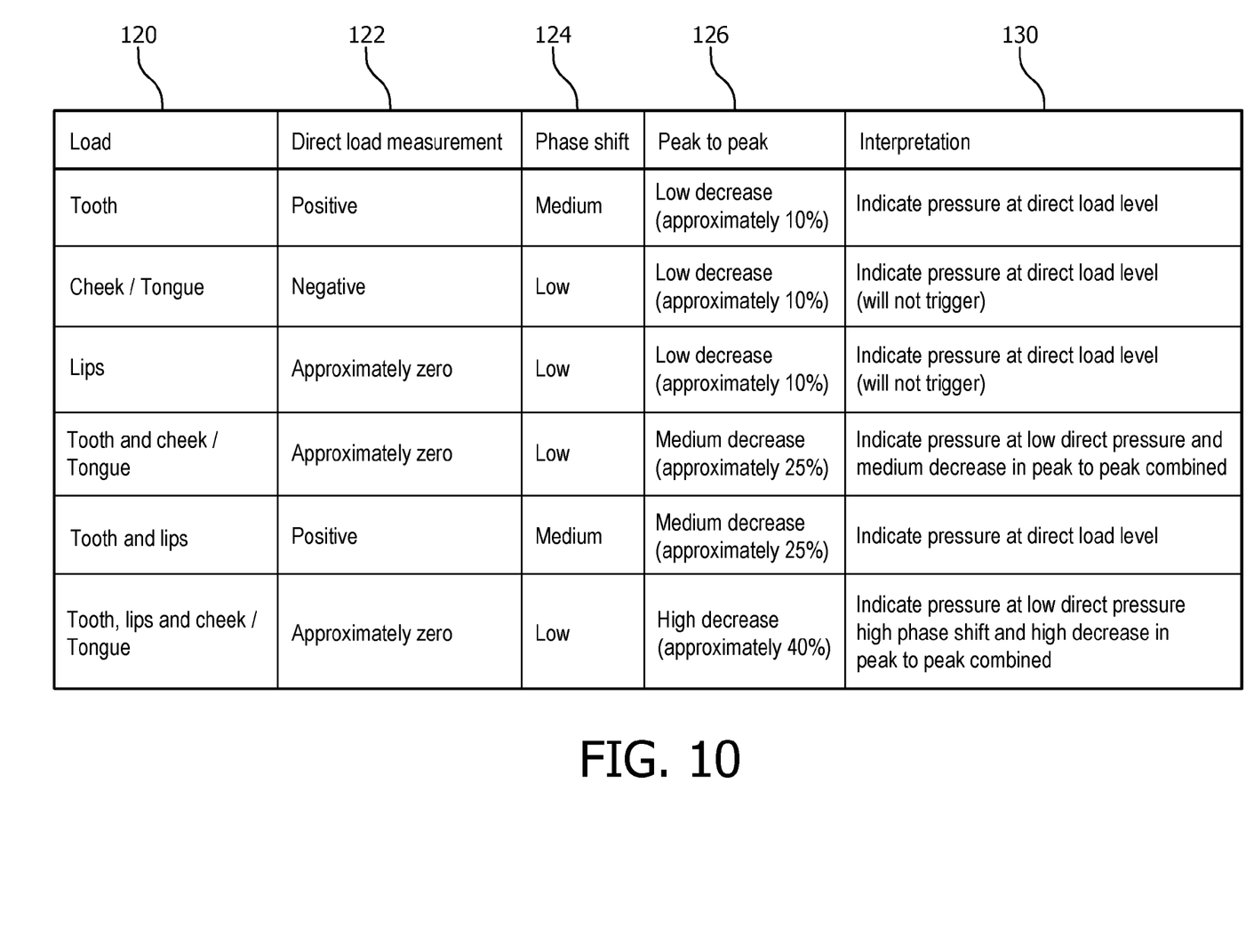
FIG. 10 is a chart which shows how the information from FIGS. 6 and 7 is used to adjust trigger point/threshold values of excessive force applied by the user.

Typically, as indicated above, the response curve is a straight line for phase shift against dynamic pressure over at least a range of pressure force of 0-300 grams. As indicated above, the results from the displacement (direct force) arrangement will provide a different result than the dynamic force (phase shift) pressure information. These two results are then compared against a table which is shown in FIG. 10, to determine the resulting effect relative to a pre-set trigger point, i.e. 300 grams, or other set value. The loads produced by the various portions of the mouth are shown in column 120. These include tooth, cheeks/tongue, lips, the combination of tooth and cheeks/tongue, the combination of tooth and lips and the combination of tooth, lips and cheeks/tongue. When the direct force or displacement load measurement is positive (column 122), the phase shift measurement is a medium value (column 124), and the peak-to-peak value (column 126) is slightly decreased, there is no change made to the trigger point which is shown in column 130. When the direct load measurement is negative, the phase shift is low, and the peak-to-peak is a low amount of decrease, there will be no trigger.

When the direct or displacement load measurement is approximately zero, the phase shift is low, and the peak to peak is a low decrease, there will be no trigger. When the direct load measurement is approximately zero, the phase shift is low and the peak to peak indicates a medium decrease, the trigger point is decreased. When the direct load measurement is positive, the phase shift is medium and the peak to peak indicates a medium decrease, the trigger point pressure remains unchanged.

When the displacement load information is approximately zero, the phase shift is low, and the peak to peak decrease is high, the trigger point will be decreased. The particular amounts in each case will depend upon the characteristics of the individual appliance. The result is more accurate information for the user relative to the use of excessive force for the bristles against the teeth and gums.

Although a preferred embodiment has been disclosed for purposes of illustration, it should be understood that various changes, modifications and substitutions may be incorporated in the preferred embodiment without departing from the spirit of the invention as defined by the claims which follow:

What is claimed is:
1. A power toothbrush with a pressure sensor, comprising:
a drive train, responsive to a drive signal, for producing a brushing action in bristles of a brushhead assembly coupled to the toothbrush;
a magnet coupled at a rear end of the drive train;
a system that includes a Hall-effect sensor for use in determining a direct force measurement of pressure applied against a user's teeth by the bristles of the brushhead assembly, wherein as force is applied to the bristles, the rear end of the drive train pivots, including the magnet, producing a lateral displacement of the magnet in a direction of the Hall-effect sensor;
a system that includes another Hall-effect sensor for use in determining a dynamic force measurement of pressure applied against the user's teeth by the bristles of the brushhead assembly, wherein the another Hall-effect sensor detects a change in phase between the drive signal and a mechanical response of the brushhead assembly produced by movement of the magnet as pressure on the bristles changes; and
a processing system responsive to the direct force measurement of pressure and the dynamic force measurement of pressure for adjusting a trigger point as either of unchanged or decreased relative to a pre-set trigger point of 300 grams or other set value, wherein the trigger point corresponds to an amount of pressure indicative of an excessive bristle force applied against the user's teeth relative to dynamic loads produced by various portions of a user's mouth.

2. The power toothbrush of claim 1, wherein the direct force measurement is a displacement measurement that includes use of a table of information in the form of response curve which relates a voltage output of the Hall-effect sensor to a displacement of the magnet, further which corresponds to force applied to the bristles of the brushhead assembly.

3. The power toothbrush of claim 2, wherein determining the direct force measurement of pressure further includes determining displacement information on via the Hall-effect a sensor and magnet.

4. The power toothbrush of claim 3, wherein the Hall-effect sensor of the system for use in determining the direct force measurement of pressure is mounted within a changing magnetic field produced by the magnet at the rear end of a drive train, wherein an output signal of the Hall-effect sensor changes from a no-load condition as a function of a displacement of the rear end of the drive train due to pressure on the brush element bristles of the brushhead assembly, and wherein the processing system is further responsive to the Hall-effect sensor output signal and stored information to produce a signal, indicative of pressure applied to the bristles of the brushhead assembly during a brushing operation, from the displacement information.

5. The power toothbrush of claim 2, wherein responsive to the displacement measurement being positive, the processing system makes no changes to the trigger point and uses the pre-set trigger point as the trigger point.

6. The, power toothbrush of claim 2 wherein responsive to the displacement measurement being negative, the processing system uses the pre-set trigger point as the trigger point, further with no triggering of an excessive pressure warning signal.

7. The power toothbrush of claim 2, wherein responsive to the displacement measurement being approximately zero, a phase shift in an output signal of the Hall-effect sensor being low, and a peak-to-peak movement of bristle motions, as determined via the system for determining the direct force measurement of pressure or the system for determining the dynamic force measurement of pressure, decreases by 25% to a medium extent, the processing system decreases the trigger point relative to the pre-set trigger point.

8. The power toothbrush of claim 2, wherein responsive to the displacement measurement being approximately zero, a phase shift in an output signal of the Hall-effect sensor being low, and a peak-to-peak movement of bristle motions, as determined via the system for determining the direct force measurement of pressure or the system for determining the dynamic force measurement of pressure decreases by 40%, the processing system decreases the trigger point relative to the pre-set trigger point.

9. The power toothbrush of claim 1, wherein the processing system is further responsive to phase shift information in an output signal of the another Hall-effect sensor relative to a phase of the drive signal to determine the dynamic force measurement.

10. The power toothbrush of claim 9, wherein the processing system further determines a phase shift in the output signal of the another Hall-effect sensor due to load applied to the bristles (34) of the brushhead assembly during brushing operations, in accordance with stored information relating values of phase shift to load.

11. The power toothbrush of claim 10, wherein the processing system further includes a zero crossing circuit for determining the phase shift.

12. The power toothbrush of claim 9, wherein the processing system is further configured for averaging the output signal from the another Hall-effect sensor over several cycles and for filtering noise from the another Hall-effect sensor output signal.

13. The power toothbrush of claim 1, wherein displacement information determined via the system for determining the direct force measurement of pressure and phase shift information determined via the system for determining a dynamic force measurement of pressure are determined continuously.

* * * * *